United States Patent [19]

Shirafuji et al.

[11] Patent Number: 4,670,612

[45] Date of Patent: Jun. 2, 1987

[54] METHOD FOR PRODUCING ALICYCLIC ALCOHOLS

[75] Inventors: Tamio Shirafuji; Kiyomi Sakai; Itaru Kawata, all of Niihama, Japan

[73] Assignee: Sumitomo Chemical Company, Limited, Osaka, Japan

[21] Appl. No.: 869,612

[22] Filed: Jun. 2, 1986

[30] Foreign Application Priority Data

Jun. 18, 1985 [JP] Japan .................................. 60-132635
Jun. 18, 1985 [JP] Japan .................................. 60-132636

[51] Int. Cl.$^4$ ............................................. C07C 39/04
[52] U.S. Cl. .................................................... 568/899
[58] Field of Search ......................................... 568/899

[56] References Cited

U.S. PATENT DOCUMENTS

| 4,236,034 | 11/1980 | Aoshima et al. | 568/899 |
| 4,456,776 | 6/1984 | Neier et al. | 568/899 |
| 4,469,905 | 9/1984 | Inwood et al. | 568/899 |
| 4,528,401 | 7/1985 | Yeh et al. | 568/899 |

FOREIGN PATENT DOCUMENTS 706436 3/1965 Canada ................................ 568/899

OTHER PUBLICATIONS

Chemical Abstracts, 70, 57279x., Matsumoto et al.
Chemical Abstracts, 100, 5938e.
Chemical Abstracts, 102, 78434p.

*Primary Examiner*—Werren B. Lone
*Attorney, Agent, or Firm*—Stevens, Davis, Miller & Mosher

[57] ABSTRACT

A method for producing alicyclic alcohols by the hydration of olefins in the presence of an aromatic sulfonic acid, which comprises incorporating molybdic acid or its salt and/or vanadium oxide, vanadic acid or its salt in the reaction system. The alicyclic alcohols are useful as intermediates for caprolactam, adipic acid, insecticides, etc.

7 Claims, No Drawings

METHOD FOR PRODUCING ALICYCLIC ALCOHOLS

The present invention relates to a method for producing alicyclic alcohols useful as intermediates for caprolactam, adipic acid, insecticides, etc., and solvents for resins, rubbers, etc. More particularly, the present invention relates to an industrially excellent improvement in a method for producing alicyclic alcohols by the hydration of olefins in the presence of an aromatic sulfonic acid.

A method for producing alicyclic alochols by the hydration of olefins in the presence of an aromatic sulfonic acid is well known and disclosed, for example, in Japanese Patent Publication Nos. 8104/1968 and 16125/1968. Also, Japanese Patent Application Kokai (Laid-open) Nos. 121229/1983 and 193836/1984 disclose that this reaction is carried out in the presence of a heteropolyacid.

In this method for producing alicyclic alcohols, the commonly used materials for the apparatus are not suitable because aromatic sulfonic acids have a very strong corrosive action. Consequently, there must be used expensive materials such as Hastelloy C, or glasslined or fluorocarbon resin-lined materials, which become a problem in terms of economy when this reaction is carried out on commercial scales. Also, reduction in the corrosive action has been tried by using a heteropolyacid in the system, but the corrosion resistance obtained is not always satisfactory.

In view of this situation, the present inventors extensively studied a method for producing alicyclic alcohols with good efficiency by the hydration of olefins in the presence of an aromatic sulfonic acid, and as a result, found that a very large anticorrosive effect is obtained by incorporating molybdic acid or its salt and/or vanadium oxide, vanadic acid or its salt in this reaction system, and besides that the catalytic activity of the aromatic sulfonic acid is improved by the presence of such additives. The present inventors thus completed the present invention.

According to the present invention, there is provided a method for producing alicyclic alcohols by the hydration of olefins in the presence of an aromatic sulfonic acid, characterized in that molybdic acid or its salt and/or vanadium oxide, vanadic acid or its salt are incorporated in the reaction system.

Preferred olefins used as a material in the method of the present invention are cyclic olefins having not more than 12 carbon atoms. The cyclic olefins include for example cyclopentene, cyclohexene, cyclooctene, 1,5-cyclooctadiene, cyclododecene, 1,5,9-cyclododecatriene, etc.

The aromatic sulfonic acid used in the method of the present invention includes, for example, benzenesulfonic acid, p-toluenesulfonic acid, naphthalenesulfonic acid, dodecylbenzenesulfonic acid, naphthosulfonic acid, etc. Also, sulfonic acid-type ion exchange resins such as polystyrenesulfonic acid may be used.

The amount of this aromatic sulfonic acid used is generally about 0.01 to about 10 moles based on 1 mole of the olefin.

In the method of the present invention, molybdic acid added to the reaction system includes, for example, $MoO_3$, $MoO_3 \cdot H_2O$, $MoO_3 \cdot 2H_2O$, etc. The salt of molybdic acid includes, for example, $(NH_4)_2MoO_4$, $K_2MoO_4$, $CaMoO_4$, $Na_2MoO_4$, etc.

In the method of the present invention, vanadium oxide added to the reaction system includes, for example, $V_2O_5$. Vanadic acid includes, for example, $V_2O_5 \cdot H_2O$, $V_2O_5 \cdot 2H_2O$, $HVO_4$, etc. The salt of vanadic acid includes, for example, $NH_4VO_3$, $NaVO_3$, $KVO_3$, $Na_3VO_4$, $Na_3VO_4 \cdot 16H_2O$, $Na_4V_2O_7$, $K_4V_2O_7$, etc.

These molybdic acid or its salt, vanadium oxide and vanadic acid or its salt may be used alone or in mixture of two or more of them.

In the present invention, these molybdic acid or its salt and/or vanadium oxide, vanadic acid or its salt are generally used in amounts of about 0.001 to about 5 wt. % based on the aromatic sulfonic acid. When the amount is less than the above range, there is little improvement in the anticorrosive and catalytic activity. If the amount exceeds the above range, a sufficient effect enough to correspond to such amount is not obtained.

In the method of the present invention, a corrosion inhibitor other than molybdic acid or its salt and/or vanadium oxide, vanadic acid or its salt may be added. Such corrosion inhibitor includes for example hexavalent chromium, phosphoric acid, etc.

The amount of water used in the method of the present invention is generally about 0.1 to about 100 moles based on 1 mole of the olefin.

The reaction temperature in the method of the present invention is generally about 50° to about 200° C., preferably 70° to 150° C. Reaction temperatures lower than 50° C. retard the reaction rate so that they are not practical. Reaction temperatures higher than 200° C. are disadvantageous in terms of the equilibrium of the reaction.

The reaction pressure in the method of the present invention is preferably higher than the pressure necessary to keep the olefin to in the liquid phase under the reaction condition. But, a pressure under which the olefin is sufficiently dissolved in the reaction solution also will do. The pressure can also be controlled by the use of inert gases such as a nitrogen gas.

The method of the present invention is an industrially excellent method for producing alicyclic alcohols by the hydration of olefins in the presence of an aromatic sulfonic acid in which a very large anticorrosive effect is obtained by incorporating molybdic acid or its salt and/or vanadium oxide, vanadic acid or its salt in the reaction system, so that little or no corrosion is observed for the commonly used materials such as SUS-304, SUS-316 and SUS-316L, and besides in which an improvement in the catalytic activity of the aromatic sulfonic acid is obtained.

The method of the present invention will be illustrated more specifically with reference to the following examples wherein cyclohexanol is produced with cyclohexene as the starting material. But, the present invention is not limited to these examples. Hereafter, the conversion and selectivity used in the illustration are values obtained from the following equations.

$$\text{Conversion (\%)} = \frac{\text{Number of moles of consumed cyclohexene}}{\text{Number of moles of fed cyclohexene}} \times 100$$

$$\text{Selectivity (\%)} = \frac{\text{Number of moles of formed cyclohexanol}}{\text{Number of moles of consumed cyclohexene}} \times 100$$

EXAMPLE 1

To a 10-ml glass ampoule were added 0.04 g of molybdenum tri-oxide, 2 g of a 75% aqueous p-toluenesulfonic acid solution and 0.6 g of cyclohexene, and after sealing the ampoule, the mixture was heated to carry out reaction at 110° C. for 30 minutes. After cooling, the ampoule was opened, and the reaction solution was taken out, made homogeneous with addition of ethanol and neutralized with a 30% aqueous NaOH solution. The solution obtained was quantitatively measured for cyclohexene and cyclohexanol by gas chromatography to obtain as a result that the conversion was 24.9% and the selectivity was 98.3%.

EXAMPLE 2

Procedure was carried out in the same manner as in Example 1 except that 0.04 g of vanadium pentoxide was used in place of molybdenum trioxide. As a result, it was found that the conversion was 22.1% and the selectivity was 97.7%.

COMPARATIVE EXAMPLE 1

Procedure was carried out in the same manner as in Example 1 except that molybdenum trioxide was not added to obtain as a result that the conversion was 24.2% and the selectivity was 75.0%.

COMPARATIVE EXAMPLE 2

Procedure was carried out in the same manner as in Example 1 except that 0.04 g of phosphomolybdic acid was used in place of molybdenum trioxide to obtain as a result that the conversion was 22.3% and the selectivity was 97.7%.

EXAMPLE 3

To a 1-liter glass autoclave were added 6 g of molybdenum tri-oxide, 300 g of a 67% aqueous p-toluenesulfonic acid solution and 100 g of cyclohexene. After performing reaction at 120° C. for 1 hour, the autoclave was cooled, and the reaction solution was taken out and separated into aqueous and oily layers. Each layer was quantitatively measured for cyclohexene and cyclohexanol to obtain as a result that the conversion was 55.7% and the selectivity was 92.6%.

COMPARATIVE EXAMPLE 3

Procedure was carried out in the same manner as in Example 3 except that molybdenum trioxide was not added to obtain as a result that the conversion was 45.2% and the selectivity was 92.9%.

EXAMPLE 4

To a 35-ml glass ampoule were added a SUS 316L test piece, 0.32 g of molybdenum trioxide and 16 g of a 60% aqueous p-toluenesulfonic acid solution. After sealing the ampoule, the mixture was heated to 110° C. for 100 hours. After cooling, the ampoule was opened, and the test piece was taken out and measured for the corrosion rate. As a result, it was found that the corrosion rate was 0.004 g/m$^2$·hr.

EXAMPLE 5

Procedure was carried out in the same manner as in Example 4 except that the amount of molybdenum trioxide was changed to 0.087 g to obtain as a result that the corrosion rate was 0.007 g/m$^2$·hr.

COMPARATIVE EXAMPLE 4

Procedure was carried out in the same manner as in Example 4 except that molybdenum trioxide was not added to obtain as a result that the corrosion rate was 1.766 g/m$^2$·hr.

COMPARATIVE EXAMPLE 5

Procedure was carried out in the same manner as in Example 4 except that 0.32 g of phosphotungstic acid was added in place of molybdenum trioxide to obtain as a result that the corrosion rate was 1.555 g/m$^2$·hr.

COMPARATIVE EXAMPLE 6

Procedure was carried out in the same manner as in Example 4 except that 0.32 g of phosphomolybdic acid was added in place of molybdenum trioxide to obtain as a result that the corrosion rate was 0.009 g/m$^2$·hr.

EXAMPLE 6

To a 35-ml glass ampoule were added a SUS 304 test piece, 0.32 g of vanadium pentoxide and 16 g of a 60% aqueous p-toluenesulfonic acid solution. After sealing the ampoule, the mixture was heated to 110° C. for 92 hours. After cooling, the ampoule was opened, and the test piece was taken out and measured for the corrosion rate. As a result, it was found that the corrosion rate was 0.006 g/m$^2$·hr.

COMPARATIVE EXAMPLE 7

Procedure was carried out in the same manner as in Example 6 except that vanadium pentoxide was not added to obtain as a result that the corrosion rate was larger than 1 g/m$^2$·hr.

COMPARATIVE EXAMPLE 8

Procedure was carried out in the same manner as in Example 6 except that 0.32 g of phosphomolybdic acid was added in place of vanadium pentoxide to obtain as a result that the corrosion rate was 0.010 g/m$^2$·hr.

EXAMPLE 7

To a 1-liter glass autoclave were added 120 g of naphtholsulfonic acid, 270 g of water and 100 g of cyclohexene. After performing reaction at 110° C. for 3 hours, the autoclave was cooled, and the reaction solution was taken out and separated into aqueous and oily layers. To a 35-ml glass ampoule were added a SUS 316L test piece, 0.2 g of molybdenum trioxide and 10 g of the above aqueous layer. After sealing the ampoule, the mixture was heated to 110° C. for 74 hours. After cooling, the ampoule was opened, and the test piece was taken out and measured for the corrosion rate. As a result, it was found that the corrosion rate was 0.020 g/m$^2$·hr.

COMPARATIVE EXAMPLE 9

Procedure was carried out in the same manner as in Example 7 except that molybdenum trioxide was not added to obtain as a result that the corrosion rate was larger than 1 g/m$^2$·hr.

What is claimed is:

1. In the method for producing alicyclic alcohols by the hydration of cycloolefins having not more than 12 carbon atoms with water using an aromatic sulfonic acid as a catalyst at a temperature in the range from about 50° to about 200° C., the improvement which comprises carrying out said hydration in the presence of at least one member selected from the group consisting of molybdic acid, molybdic acid salt, vanadium oxide, vanadic acid and vanadic acid salt in the reaction system.

2. The method according to claim 1, wherein the cycloolefin is cyclopentene, cyclohexene, cyclooctene 1,5-cyclooctadiene, cyclododecene, or 1,5,9-cyclododecatriene.

3. The method according to claim 1, wherein the amount of said at least one member is from about 0.001 to about 5% by weight based on the aromatic sulfonic acid.

4. The method according to claim 1, wherein the salt of molybdic acid or vanadic acid is an ammonium salt or an alkali metal salt.

5. The method according to claim 1, wherein the amount of water is from about 1 to about 100 moles based on 1 mole of the cycloolefin.

6. The method according to claim 1, wherein the aromatic sulfonic acid is selected from the group consisting of benzenesulfonic acid, p-toluenesulfonic acid, naphthalenesulfonic acid, dodecylbenzenesulfonic acid, naphtholsulfonic acid and polystyrenesulfonic acid.

7. The method according to claim 1, wherein the amount of the aromatic sulfonic acid is from about 0.01 to about 10 moles based on 1 mole of the cycloolefin.

* * * * *